United States Patent [19]

Pike

[11] Patent Number: 5,475,201
[45] Date of Patent: Dec. 12, 1995

[54] METHOD FOR IDENTIFYING A DIFFUSELY-REFLECTING MATERIAL

[75] Inventor: John N. Pike, Pleasantville, N.Y.

[73] Assignee: Black & Decker Inc., Newark, Del.

[21] Appl. No.: 1,380

[22] Filed: Feb. 25, 1993

[51] Int. Cl.[6] .............................. H05B 1/02; D06F 75/26
[52] U.S. Cl. .......................... 219/497; 219/250; 219/252; 219/501; 250/559.01
[58] Field of Search ................................... 219/388, 497, 219/250–252, 501, 506, 488, 494; 250/571, 572, 550, 554; 34/89, 48, 43

[56] References Cited

U.S. PATENT DOCUMENTS

| | | | |
|---|---|---|---|
| 3,747,755 | 7/1973 | Senturia et al. | 209/111.5 |
| 3,803,383 | 4/1974 | Fresard et al. | 219/243 |
| 4,980,981 | 1/1991 | Naidoo | 38/1 C |
| 5,119,132 | 6/1992 | Butler | 355/208 |
| 5,156,025 | 10/1992 | Frucco | 68/12.02 |
| 5,252,836 | 10/1993 | Matthews et al. | 250/571 |
| 5,308,992 | 5/1994 | Crane et al. | 250/556 |

FOREIGN PATENT DOCUMENTS

| | | | |
|---|---|---|---|
| 0100399 | 2/1984 | European Pat. Off. | |
| 0523793 | 1/1993 | European Pat. Off. | 219/497 |

OTHER PUBLICATIONS

Some Industrial Applications of FT–IR Diffuse Reflectance Spectroscopy Journal Of The Textile Institute Article.
A Reflectometer For Measuring Diffuse Reflectance in the Visible And Infrared Regions.
G. Celikiz, "Textiles", *Practical Spectroscopy*, 701–713, Ch. 10 (1977).
L. Müller–Gerbes, "Messung der Farbe von Textilien mit optischen Geräten", *Spinner und Weber Textilveredlung*, 44–48, 340–344 (1960).
Timo Hyvarinen and Pentti Niemela, "Rugged multiwavelength NIR and IR analyzers for industrial process measurements", *SPIE*, vol. 1266, In–Process Optical Measurements and Industrial Methods, pp. 99–104 (1990).
R. W. Frei, J. D. MacNeil, "Diffuse Reflectancce Spectroscopy in Environmental Problem–Solving", CRC Press, pp. 102–104 and 106.
R. S. Davidson, Doreen King, "A New Method of Distinguishing Wool from Polyester–fibre and Cotton Fabrics", *J. Text. Inst.*, No. 6, pp. 382–384 (1983).
Willard L. Derksen, Thomas I. Monahan, "A Reflectometer for Measuring Diffuse Reflectance in the Visible and Infrared Regions", *Journal of the Optical Society of America*, 42:263–265 (Apr. 1952).
K. D. Klapstein, F. L. Weichman, Will N. Bauer, D. J. Kenway, "Optical characteristics of wood stains and rot", *Applied Optics*, 28:4450–4452 (Oct. 1989).
Michael J. Resso, Richard E. Harris, "The Hunt For Cost–Effective IR Transducers", *Photonics Spectra*, pp. 111–116 (Apr. 1990).
R. F. Edgar, P. H. Hindle, "Infrared Absorption Gauging—The Future", *SPIE*, vol. 665, Optical Techniques for Industrial Inspection, pp. 101–109 (1986).
Howard J. Goldner, "Near IR Opens A Window To Rapid Analysis", *R&D Magazine*, pp. 56–60 (May 1991).
John N. Pike, "Modulation of subminiature tungsten–halogen lamps", *Applied Optics*, 29:903–904 (Mar. 1990).

*Primary Examiner*—Mark H. Paschall
*Attorney, Agent, or Firm*—Barry E. Deutsch

[57] ABSTRACT

An apparatus and method is provided for identifying a diffusely-reflecting material, such as a textile fabric. A light source transmits radiation onto the unknown material, and a detector receives radiation diffusely reflected by the unknown material, and generates signals indicative of diffuse-reflection characteristics of the unknown material. A processor is coupled to the detector, and includes diffuse-reflection data on a plurality of reference materials. The processor compares the diffuse-reflection characteristics of the unknown material based on the signals of the detector to the reference data, and by a process of elimination, identifies the unknown material.

6 Claims, 6 Drawing Sheets

1

METHOD FOR IDENTIFYING A DIFFUSELY-REFLECTING MATERIAL

FIELD OF THE INVENTION

The present invention relates to methods and apparatus for optical sensing, and more particularly, to such methods and apparatus employing infrared, diffuse-reflection spectroscopy for sensing and classifying diffusely-reflecting materials.

BACKGROUND INFORMATION

There have been various uses of spectroscopy for characterizing or understanding the make-up of materials. A test technique for distinguishing wool from polyester-fibre and cotton fabrics employing photoacoustic spectroscopy is discussed in the article, Davidson and King, "A Method of Distinguishing Wool from Polyester-fibre and Cotton Fabrics", *J. Text. Inst.*, vol 74, p. 382 (1983). This technique makes use of the absorption spectrum of the fabric in the near infrared, which is the complement of the reflection spectrum. A major disadvantage of the proposed technique is the inability to control the resonant cell's sample wall in real-use conditions.

Another article, Derkson and Monahan, "A Reflectometer for Measuring Diffuse Reflectance in the Visible and Infrared Regions", *J. Opt. Soc. Am.*, Vol. 42, p. 263 (1952), discusses an instrument for measuring diffuse reflectance of materials, and employs as targets, among other things, cotton twill and wool serge. This instrument operates in the infrared, and in the visible-wavelength range for visual appearance purposes.

Another instrument is reported by Timo Hyvarinen, "Rugged Multiwavelength NIR and IR Analyzers For Industrial Process Measurements", SPIE Conference Proceedings, Vol. 1266, p. 99 (1990), European Congress on Optics, The Hague. This device is a hand-held, battery-operated meter for optically measuring the moisture content of peat. A tube is inserted into a peat bog, and a trigger is pulled in order to display the moisture measurement on a display. This device uses a miniature tungsten lamp, and a detector including two side-by-side lead-sulfide (PbS) photoconductive cells located behind interference filters peaked at 1.80 and 1.94 microns, the useful sensing bands for water. The PbS cells and interference filters are mounted in a windowed, $N_2$-filled, hermetically-sealed container, to prolong filter life. The light source is electrically modulated at 35 Hz and transmitted through a quartz window into the peat, and the radiation diffusely reflected by the peat is measured by the detector, which provides output signals indicative of the moisture content of the peat.

It would be desirable to provide a method and apparatus for identifying unknown diffusely-reflecting materials, such as textile fabrics, which preferably use optical means to sense and rapidly identify the unknown material. Although the prior art discloses devices for optically measuring a characteristic or the make-up of a diffusely-reflecting material, it has failed to provide a method and apparatus for identifying an unknown material rapidly and in real time, which preferably uses infrared spectroscopy for identifying an unknown material based on the characteristic spectrum of that material.

SUMMARY OF THE INVENTION

The present invention is directed to an apparatus for identifying a diffusely-reflecting material, such as a textile fabric. The apparatus comprises a light source for transmitting radiation onto the unknown material, and a detector for receiving radiation diffusely reflected by the unknown material, which generates signals indicative of diffuse-reflection characteristics of the unknown material. A processor of the apparatus is coupled to the detector, and includes diffuse-reflection reference data on a plurality of reference materials. The processor compares the diffuse-reflection characteristics of the unknown material to the reference data, and by a process of elimination, identifies the unknown material.

In one embodiment of the present invention, the light source is a tungsten-halogen lamp. The detector preferably includes a plurality of photoconductive cells, such as lead-sulfide (PbS) cells, and each cell generates an output signal indicative of the intensity of the diffusely-reflected radiation within a respective wavelength channel of finite bandwidth unique to that cell. This embodiment of the present invention may also comprise an interference filter located between the unknown material and the photoconductive cells, for filtering the diffusely-reflected radiation transmitted onto the photoconductive cells and defining the respective wavelength channels.

In another embodiment of the present invention, the apparatus is mounted within a household iron for identifying the material being ironed. In this instance, the processor is coupled to means for automatically controlling the temperature of the iron, such as a thermostat, based on the identity of the fabric being ironed.

The present invention is also directed to a method for identifying a diffusely-reflecting material, such as a textile fabric. The method comprises the following steps: a) transmitting radiation onto the unknown material from a light source; b) receiving at least a portion of the radiation diffusely-reflected by the unknown material with a detector, and generating signals indicative of diffuse-reflection characteristics of the unknown material; and c) comparing diffuse-reflection characteristics of the unknown material with diffuse-reflection data on a plurality of reference materials to identify, by a process of elimination, the unknown material.

In one embodiment of the present invention, the method further comprises the step of generating a plurality of signals, wherein each signal is indicative of diffuse-reflection characteristics of the unknown material within a channel corresponding to a respective wavelength. This embodiment preferably further comprises the step of generating pattern values, wherein each pattern value corresponds to a respective channel, and comparing the pattern values of the unknown material to corresponding pattern values for the reference materials, to identify the unknown material.

In one embodiment of the present invention, the method further comprises the step of generating a plurality of pattern values for each channel, wherein each pattern value is based on a respective Q-level, and each Q-level defines a range of signals above or below each respective channel signal. Preferably, each pattern value is based on whether the average value of the signals of the two next-nearest channels falls within the range defined by the respective Q-level of the respective channel signal, as will be illustrated below.

One advantage of the apparatus and method of the present invention is that they provide a means for rapidly identifying an unknown diffusely-reflecting material, such as a textile fabric, optically, without damaging or otherwise destroying any portion of the unknown material. Another advantage of the present invention is that because it employs infrared spectroscopy, it is particularly suitable for identifying textile fabrics, since most dyes used in fabrics are non-absorbing in the infrared, and therefore the visual color of the fabric will not affect the ability of the present invention to identify that fabric. Yet another advantage of the present invention is that it is particularly adaptable to being manufactured in a relatively low-cost, compact form, and can therefore be easily used with other appliances. For example, a significant advantage of the present invention is that it can be used with a household iron to automatically identify the fabric being ironed, and to adjust the temperature of the iron for the particular fabric (without the user even knowing what type of fabric is being ironed). This can avoid significant problems due to scorching or other damage that can occur when ironing fabrics at the wrong temperature.

Other advantages of the method and apparatus of the present invention will become apparent in view of the following detailed description and accompanying drawings.

DETAILED DESCRIPTION

Figure 1:
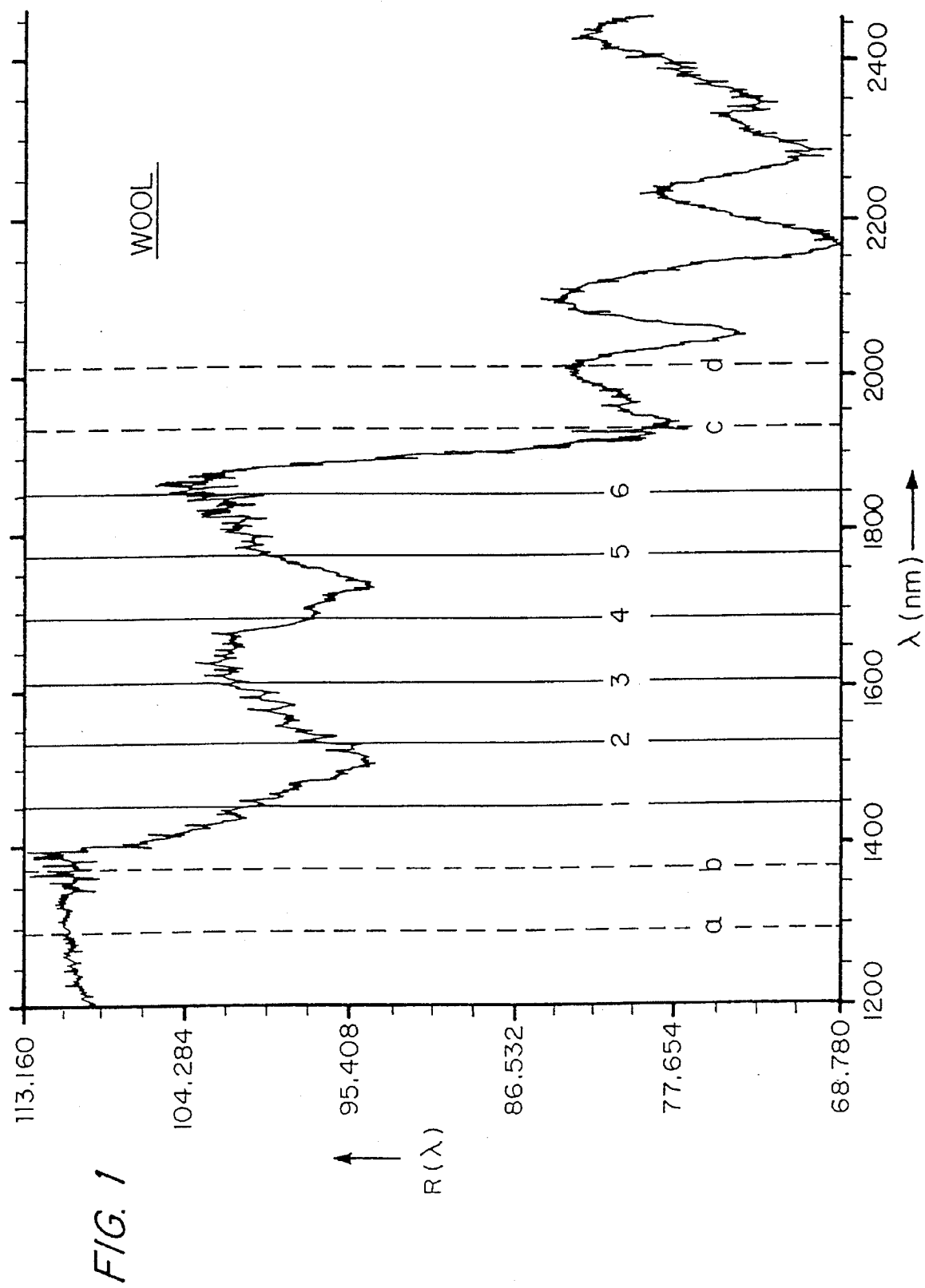
FIG. 1 is a graph illustrating the relative reflectance R(λ) of wool within the infrared spectrum of approximately 1200 nm to 2400 nm.
Figure 2:
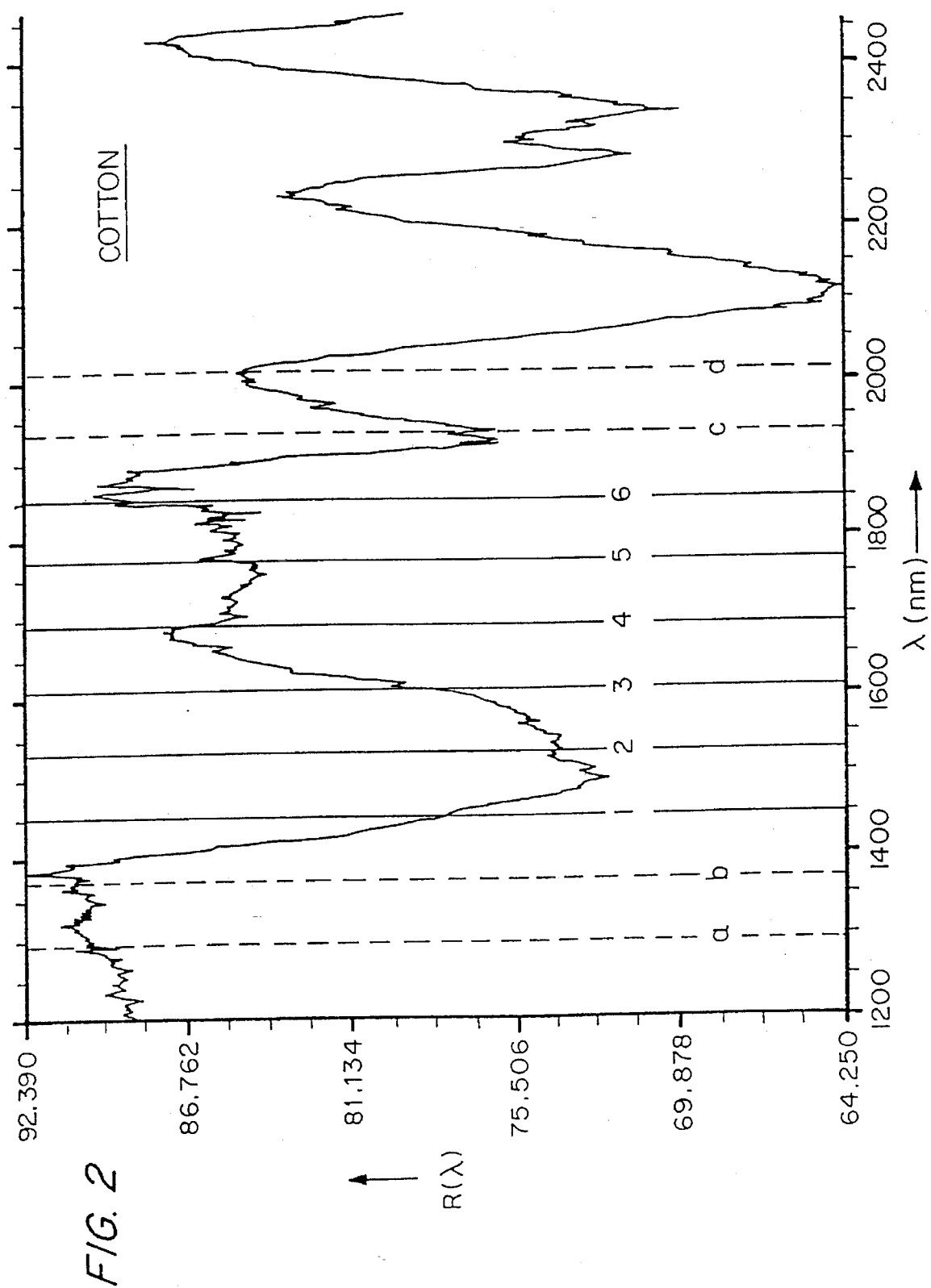
FIG. 2 is a graph illustrating the relative reflectance R(λ) of cotton within the infrared spectrum of approximately 1200 nm to 2400 nm.

It is believed that all textile materials have reasonably distinct characteristic infrared diffuse reflection spectra, at wavelengths as short as 1400 nm. FIGS. 1 and 2 are graphs illustrating the relative reflectance R(λ) of wool and cotton, respectively, within the infrared spectrum between approximately 1200 nm and 2400 nm. As can be seen, both wool and cotton (as do other textile materials) exhibit distinct diffuse-reflectance patterns. For example, wool exhibits a steep drop at approximately 1900 nm, whereas cotton exhibits a deep absorption band at approximately 1500 nm. Based on these distinctive characteristics, the method and apparatus of the present invention is able to identify an unknown fabric (or other diffusely-reflecting material), by measuring diffuse-reflectance characteristics of the unknown fabric, and comparing these characteristics of the unknown fabric to reflectance data for known fabrics in order to determine the content or type of the unknown fabric.

Figure 3:
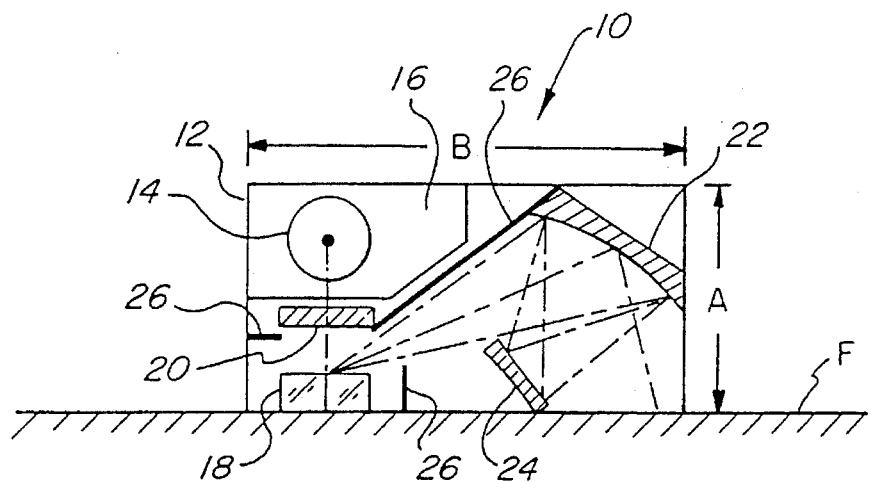
FIG. 3 is a schematic illustration of a first embodiment of an apparatus embodying the present invention for identifying an unknown diffusely-reflecting material, such as a fabric material.

In FIG. 3, an apparatus embodying the present invention for identifying a fabric F is indicated generally by the reference numeral 10. The apparatus 10 includes a housing 12, which includes a light source 14 mounted within a lamp chamber 16. The housing 12 preferably has relatively compact dimensions, so that the apparatus can be easily incorporated into other appliances, such as a household iron in order to identify the fabric being ironed, as is described further below. In the embodiment of the present invention illustrated, the dimension A is approximately 1.0 inch, the dimension B is approximately 2.0 inches, and the dimension of the housing 12 normal to the plane of the drawing (not shown) is approximately 0.5 inch. These dimensions are purely exemplary, however, and may be adjusted as technology and design considerations permit.

The light source 14 is preferably a subminiature tungsten-halogen lamp, such as the Osram HPR52 lamp, in which the filament 18 is a straight coil (oriented normal to the plane of the drawing, as shown), made from an approximately 1 mil tungsten wire wound into an approximately 0.1 mm coil diameter, which has a lighted length of approximately 1.5 mm, and a bulb diameter of less than ⅜ inch. This particular lamp is only exemplary, however, and numerous other types of light sources may equally be used. For example, Welch-Allen manufactures a gas-filled lamp with the same electrical input (2.6 V, 0.85 A) that has an approximately 0.185 inch bulb diameter. It is only desirable that the light source be an efficient emitter in the near or mid-infrared; for example, a series of LEDs, each tuned to a different wavelength, could be used instead.

When employing a subminiature tungsten-halogen lamp as the light source 14, the brightness of the lamp is preferably modulated by using half-wave rectified 60-Hz input power, in order to eliminate the need for a mechanical beam chopper to modulate the light. Half-wave rectification of subminiature tungsten-halogen lamps is described in Pike, J. N., "Modulation of subminiature tungsten-halogen lamps", *Applied Optics*, Vol. 29, No. 7, pp. 903–04 (Mar. 1, 1990). The radiation is preferably modulated in this way, so that AC detection and amplification of the diffusely-reflected radiation can be used, as is described below.

A glass component 18 is mounted in the base of the housing 12 directly beneath the light source 14, and a Fresnel lens 20 is mounted between the light source and the glass component. The Fresnel lens 20 is preferably anti-reflection coated, and made from a high-index glass with an f/# on the order of 1, in order to relay the filament brightness of the light source 14 through the glass component 18, and onto the fabric F with reasonable image formation. As shown in FIG. 3, the glass component 18 is maintained in contact with the fabric F, and serves as a visible-blocking filter to prevent visible light from entering the housing, as a fabric pressure plate, and as a slit-defining element, as is described further below.

As the radiation from the light source 14 is transmitted onto the fabric F, the infrared radiation diffusely reflected by the fabric F emerges from the top surface of the glass component 18 in all directions. An f/2 portion of this diffusely-reflected radiation is transmitted onto an ellipsoidal concave grating 22, as illustrated in FIG. 3. The grating 22 in turn transmits and disperses reflected radiation onto a sensor array 24, which in the embodiment of the present invention illustrated, is a linear array of lead-sulfide (PbS) photoconductive cells, of a type known to those skilled in the art. The grating 22 is designed to image the first-order "slit" radiation at approximately 2× demagnification onto the sensor array 24. The inside walls of the housing 12 are black, and therefore higher grating orders and the non-diffracted beam are lost in the black walls. The grating 22 is preferably a flat-field design, stamped or holographically produced on an ellipsoidal blank.

In the embodiment of the present invention illustrated, the sensor array 24 is preferably an approximately 1.0 cm array of 10 PbS photoconductive cells, which receive the focused spectrum of radiation in the wavelength range of approximately 1250 to 2050 nm. Each array element is preferably an approximately ¼ mm×5 mm slit-shaped detector, oriented normal to the plane of the drawing. Thus, each element covers approximately 20 nm of the spectrum. The space between adjacent elements of the array is equivalent to approximately 60 nm of the spectrum, which is sufficient for mounting necessary electrical connection pads (not shown). The ten photoconductive cells and their relative locations across the infrared spectrum are illustrated graphically in FIGS. 1 and 2 as "a, b, 1, 2, 3, 4, 5, 6, c, and d", wherein each letter or number represents a respective photoconductive cell channel of the sensor array 24, as is described further below.

Each cell of the sensor array 24 is preferably coupled in series with a DC input voltage (approximately 30 VDC), and is further coupled to ground through a resistor (not shown). The relatively large DC voltage across the resistor is modulated by a small AC signal voltage produced by and proportional to the intensity of the diffusely-reflected modulated radiation transmitted onto the cell within the respective bandwidth of radiation covered by that cell. The signal voltage of each cell is AC-coupled to a linear operational amplifier circuit (not shown) for amplifying and transmitting the output signal to a processor, as is described further below.

Thin black baffles 26 are placed within the housing 12 at the positions shown, in order to prevent stray light from reaching the sensor array 24. Since the stray light is also modulated at 60 Hz, its elimination is important in order to obtain accurate signals from the sensor array 24.

Figure 4:
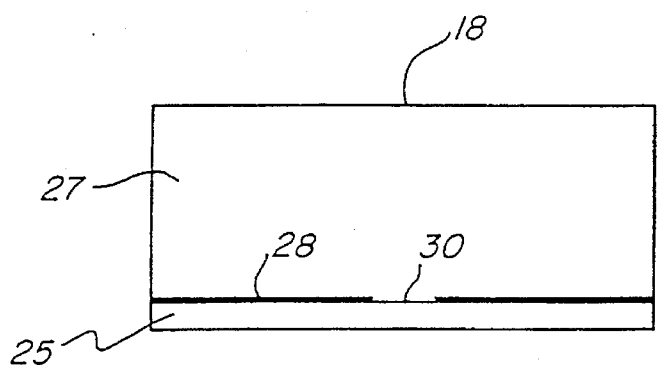
FIG. 4 is a cross-sectional view of the glass component of the apparatus of FIG. 3 which functions as a visible-blocking filter to prevent the passage of visible light into the apparatus, as a fabric pressure plate, and as a slit-defining element.

In FIG. 4, the glass component 18 is illustrated in further detail, and comprises a base layer 25 (approximately ½ mm thick) for contacting the fabric F, which is preferably made of relatively hard quartz or sapphire for durability and scratch resistance. A top portion 27 of the glass component is made from a visible-radiation absorbing material, such as Schott RG1000 "IR-Pass" glass, in order to absorb any visible radiation entering the housing 12 (e.g., radiation below approximately 1000 nm), yet permit the passage of the infrared radiation. This type of material is only exemplary, however, and any optical material known to those skilled in the art with similar optical characteristics could equally well be employed. A layer of black absorber/cement 28 is located between the top portion 27 and base layer 25, and defines an approximately 1 mm wide opening or "slit" 30 extending across the glass component (normal to the plane of the drawing), which may be filled with an optically clear cement. The 0.1 mm filament of the light source 14, imaged at approximately 1:1 magnification, fills the opening 30 in the black absorber/cement. Since a low f/# Fresnel lens 20 does not give a relatively clear image, the opening 30 is necessary to perform this function.

In the operation of the apparatus of the present invention, radiation is transmitted by the light source 14 through the Fresnel lens 20, which concentrates the radiation as it is transmitted through the opening 30 in the glass component 18 onto the fabric F. The radiation that is diffusely reflected by the fabric F is then transmitted back through the opening 30, part of which is directed onto the grating 22. The grating 22 demagnifies (by a factor of approximately 2) and directs the reflected, incident radiation onto the sensor array 24. The light source 14 is preferably operated for relatively short periods of time, in order to prevent any significant increase in temperature within the housing 12.

The ten photoconductive cells of the sensor array 24 are small side-by-side strips of IR-sensitive material, in this case, lead sulfide (PbS), as described above. When infrared radiation anywhere in the region of interest for the respective cell (each cell covers an approximately 20 nm bandwidth) is transmitted onto the cell, its resistance drops, and for relatively small signals, the change in resistance is proportional to the intensity of the diffusely-reflected infrared radiation. The ten photoconductive cells (or array elements) receive ten separate and distinct wavelength channels in the infrared, substantially equally spaced along the wavelength axis, as shown, for example, as "a, b, 1, 2, 3, 4, 5, 6, c and d", in FIGS. 1 and 2. Each cell does not measure the intensity of a single wavelength in the infrared beam, but rather receives a small range of wavelengths, the extent of which is based in part on the width of the respective cell. This range is referred to as the "spectral bandwidth" of the cell. The higher the bandwidth, the greater is the signal from each cell, which is electronically desirable. The smaller the bandwidth, however, the greater is the ability to sense rapid changes in the reflectance spectrum. In the embodiments of the present invention illustrated, spectral bandwidths in the range of approximately 10 to 30 nm provide satisfactory results.

It is noted that after the apparatus 10 is assembled, it is desirable to adjust the sensor array 24 by exposing the sensor array to the reflectance of a perfectly white target (i.e., the target material has substantially the same diffuse reflectance at all wavelengths) of radiation transmitted by the light source 14. The feedback resistors in the output amplifiers for the cells (not shown) are then adjusted (trimmed) so that the signals from all ten channels (or cells) are the same. This factory adjustment facilitates the ability of the sensor array 24 to provide accurate measurements over the life of the apparatus, regardless of drift in the output of the light source 14 over time.

Thus, the output signal of each cell of the sensor array 24 is proportional to the intensity of the diffusely-reflected radiation within the spectral bandwidth of the respective cell. These signals are preferably transmitted to a processor (not shown) and compared to reference reflectance data for a multitude of known fabric materials. By a process of logical elimination, the processor is able to determine the content or type of the fabric F, as is described further below.

Figure 5:
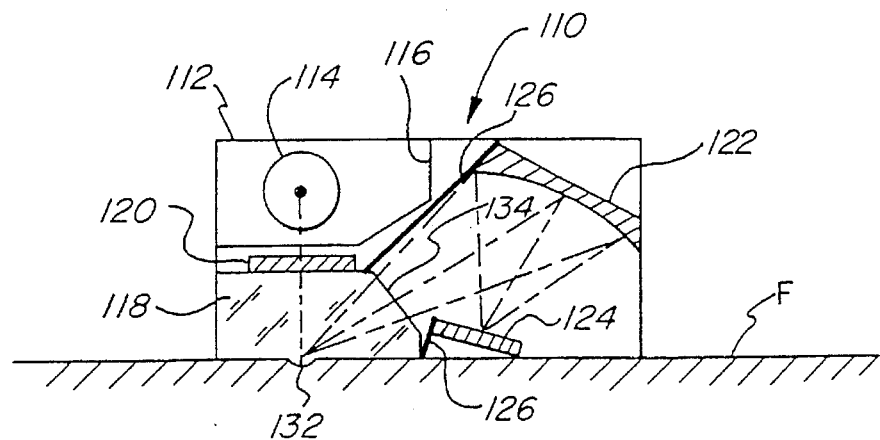
FIG. 5 is a schematic illustration of another embodiment of an apparatus embodying the present invention, in which the glass component defines a raised portion protruding from the base of the housing to prevent the collection of dust or other particles on the face of the glass component.

In FIG. 5, another embodiment of the present invention is indicated generally by the reference numeral 110. The apparatus 110 is similar to the apparatus 10 described above in connection with FIGS. 1 and 2, and therefore like reference numerals preceded by the numeral 1 are used to indicate like elements. As can be seen, the apparatus 110 differs from the embodiment described above essentially in the construction of the glass component 118 and the location of the sensor array 124.

The glass component 118 defines a ridge 132, which protrudes from the base of the housing 112 into contact with the fabric F, and extends longitudinally along the base layer 124 of the glass component (normal to the plane of the drawing). The ridge 132 is approximately 1 mm wide, and the base of the housing is opaque surrounding the ridge, so that the ridge effectively replaces the slit 30 described above in connection with the previous embodiment. The opaque surfaces surrounding, and thus defining the "slit" of the ridge 132, may be formed by a wear-resistant black coating. One side of the glass component 118 defines a viewing window 134 oriented at an acute angle with respect to the vertical axis of the housing 112, and facing the ellipsoidal grating 122. The radiation that is diffusely reflected by the fabric F and transmitted back into the glass component 118, is partially transmitted through the angled viewing window 134 and directly onto the grating 122. The grating 122 focuses and disperses the diffusely-reflected radiation onto the sensor array 124, which in turn generates output signals proportional to the intensity of the radiation in each of the 10 spectral bandwidths of interest.

One advantage of this particular construction, is that the protruding shape of the ridge 132 prevents the collection of dust particles, for example, on the surface of the glass component as it is passed over the fabric F, and thus avoids the scattering of any bright input light normally associated with such particles or similar debris located on the face of the glass component 118. Furthermore, any dust that might accumulate on the upper surface of glass component 118 is above the field of view of grating 122, so it cannot contribute to any unwanted scattering signal. Finally, glass surface 134 is in a dust-free compartment of the sensor. Since any scattered light would be modulated at 60 Hz (the same as the diffusely-reflected light), a degradation of signal quality from the sensor array 124 could occur. Hence, the construction of the present invention illustrated in FIG. 5 essentially eliminates any such scattering altogether.

Figure 6:
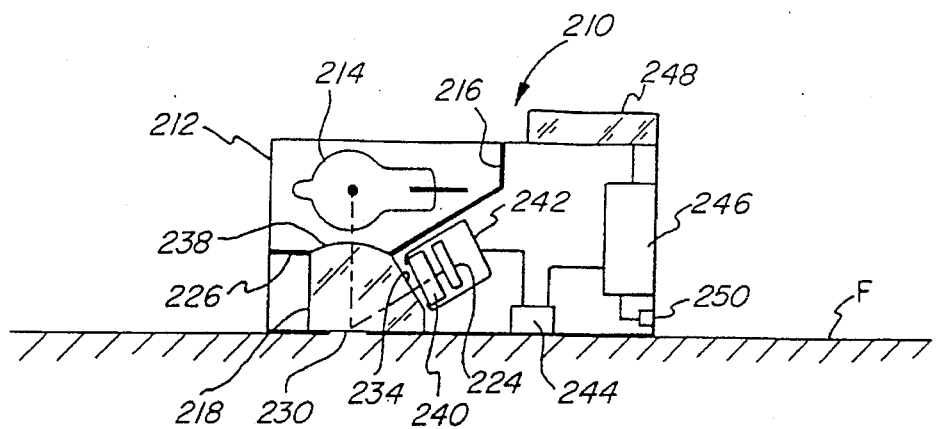
FIG. 6 is a schematic illustration of another embodiment of an apparatus embodying the present invention, employing a stepped interference filter and sensor array for measuring the intensity of the radiation diffusely reflected by the fabric (or other diffusely-reflecting material).

In FIG. 6, another embodiment of the present invention is indicated generally by the reference numeral 210. The apparatus 210 is similar to the apparatus described above in connection with FIGS. 3 through 5, and therefore like reference numerals preceded by the numeral 2 are used to indicate like elements. The embodiment of FIG. 6 differs from the embodiments described above essentially in that it does not employ focusing optics between the diffusely-reflecting material and the sensor array, but rather employs a linear-stepped interference filter and a matching PbS sensor array, both preferably contained in a hermetically sealed container.

The glass component 218 defines an angled viewing window 234, which is nominally flat, and a generally cylindrical top surface 238. As described above, the component 218 may be formed from any suitable optical material, and the viewing window 234 may be fire-polished smooth. The radius of curvature of the surface 238 is selected to "image" or concentrate the radiation from the light source 214 onto the fabric F. It is desirable to concentrate the radiation onto the fabric in order to increase the intensity of the radiation, yet maintain a relatively constant intensity across the patch being transmitted onto the fabric. The opening 230 is formed in the same manner as the opening 30 described above in connection with FIG. 4; however, it may be larger, approximately 0.2 inch wide and at least 1 cm long. Since the area being illuminated is a relatively broad, long patch in comparison to the embodiments described above, a longer filament in the light source 214 may be preferable. Also, since the area of the fabric being illuminated is relatively large, tolerances on filament shape and position can be considerably relaxed. As will also be recognized by those skilled in the art, the opening may equally be formed by employing a ridge, as described above in connection with FIG. 5.

The infrared radiation diffusely reflected from the fabric F is transmitted through the opening 230 in all directions. The portion transmitted through the angled viewing window 234, passes through a stepped interference filter 240, and is transmitted directly onto the sensor array 224. Both the interference filter 240 and the sensor array 224 are oriented normal to the plane of the drawing, and the spacing of the array elements (PbS photoconductive cells) substantially matches the spacing of the steps of the interference filter 240, so that each array element is aligned with a respective step in the interference filter. Each step in the interference filter 240 has peak transmission within the desired spectral bandwidth of the corresponding photoconductive cell, and the bandwidth is on the order of approximately 50 nm.

Both the interference filter 240 and the sensor array 224 are preferably hermetically sealed in a metal container 242 to lengthen both filter and photoconductive cell lives. The front face of the interference filter 240 (adjacent the viewing window 234) is formed by the quartz base upon which the multi-layer filters are deposited, and is preferably coated with a conductive coating reasonably transparent in the wavelength range of interest, which in this case is approximately 1400 to 2100 nm. This can be done, for example, by employing an indium-tin oxide formulation, in which the plasma edge is just beyond 2100 nm. The conductive coating provides electrical shielding against stray 60 Hz energy emanating from the lamp chamber 216. Preferably, the load resistors for each photoconductive cell are laser-trimmed and located within the container 242.

As also shown in FIG. 6, the output leads of the sensor array 224 are coupled to a signal conditioning circuit 244, which preferably includes the linear operational-amplifier circuits AC-coupled to the load resistors (not shown) of the photoconductive cells. As described above, each photoconductive cell transmits an output signal proportional to the intensity of the diffusely-reflected radiation within the spectral bandwidth of the respective cell. The signal conditioning circuit 244 digitizes each output signal, and in turn transmits the signals to a processor 246. The processor 246 has a stored database of diffuse-reflection data on the known fabric materials of interest, and compares data based on the output signals of the sensor array 224 to the known diffuse-reflection data. By a process of elimination, the processor 246 is able to effectively determine the material of the fabric F by comparing the data based on the output signals to the known data, as is described further below.

The processor 246 is also coupled to a display 248 to display either a numerical value or to simply indicate the type of fabric F under consideration, e.g., "cotton", "wool", "cotton/polyester", etc. An output port 250 is also coupled to the processor 246 to drive, for example, a remote display (not shown). It is noted that the signal conditioning circuit, processor and display of FIG. 6 can equally be employed with the embodiments of the present invention illustrated in FIGS. 3–5, in a manner known to those skilled in the art. It is also noted that a filtered sensor array as shown in FIG. 6 can be substituted for the unfiltered arrays 24 and 124 of the embodiments shown in FIGS. 3 and 5, respectively, wherein the concave gratings 22 and 122, respectively, are replaced by simple ellipsoidal mirrors.

As will be recognized by those skilled in the art, the apparatus of the present invention not only can be employed as a hand-held instrument for sensing and classifying diffusely-reflecting materials, such as fabrics, as shown in FIG. 6, but can equally be useful in other devices, such as household appliances. For example, in FIG. 7, the apparatus 210 is shown mounted within a household iron for ironing clothes so that the opening 230 is located in the heel of the iron. In this embodiment of the present invention, rather than being coupled to a display, the processor 246 is coupled to means 252 for automatically controlling the temperature of the iron, such as a thermostat. The iron is turned up so that the heel (and opening 230) is seated on the fabric F, and the processor 246 determines the type of material of the fabric based on its diffuse-reflection spectra. The processor 246 then automatically adjusts the thermostat 252 to set the iron at an appropriate temperature for that particular fabric.

It is noted that in this embodiment of the present invention, it may be possible to employ a sensor array 224 with fewer than 10 photoconductive cells. When ironing fabrics, numerous types of fabric can be ironed at the same iron temperature. For example, both cotton and linen may be ironed at approximately the same temperature. Therefore, the sensor array 224 need not have so many channels as to permit differentiation among all such fabrics which can be ironed at the same temperature, but rather need only be sensitive enough to distinguish between groups of fabrics. A sensor array with as few as six photoconductive cells could be sufficiently satisfactory for this purpose.

In accordance with the method of the present invention, an unknown fabric F (or other diffusely reflecting material) is identified based on the output signals of the signal array (i.e., the fabric's diffuse-reflection spectrum). As described above, the sensor array is a linear array of separate but substantially equal IR-sensitive elements spread along the wavelength axis, as indicated in the graphs of FIGS. 1 and 2. The ten elements are represented by the vertical lines, "a, b, 1, 2, 3, 4, 5, 6, c and d", each one being separated from its neighbor by approximately 80 nm. The central six elements ("1, 2, 3, 4, 5 and 6") are referred to as the "decision" channels, whereas the remaining channels ("a, b, c and d") are referred to as the "outer" channels. In accordance with the present invention, the signal at each decision channel is compared with the average of the signals from the two next-nearest neighbors of that channel to obtain "pattern values" for each fabric. For example, the processor 246 compares the signal of channel 1 to the average of the channel a and channel 3 signals, and determines whether this comparison is significantly greater than unity, significantly less than unity, or not significantly different at all. This decision process is performed for each of the decision channel signals, and the results of this decision process (the "pattern values") are compared to the pattern values for known reference fabrics stored in a library of pattern values to identify the fabric under consideration.

Accordingly, in order for the apparatus of the present invention to be able to identify a large number of fabrics (or other diffusely-reflecting materials) the processor 246 must have in its database or library sufficient reference data (pattern values) on each of the many different fabrics (or other diffusely-reflecting materials) likely to be encountered by a user. In the embodiment of the present invention illustrated, there are J fabrics in the library, and for each of the J reference fabrics, there are approximately three tables of "pattern values" stored in memory.

As one example, the three tables of reference pattern values for wool are illustrated below, and can be generated based on the data for wool illustrated in FIG. 1. For example, as shown in FIG. 1, channel 6 generates a signal of approximately 103, channel 4 (one next-nearest neighbor) generates a signal of approximately 98, and channel d (the other next-nearest neighbor) generates a signal of approximately 83. The average of the two signals of the next-nearest neighbors (4 and d) is approximately 90.5. It is then determined: Is the center signal Q% higher or lower than the average of the two next-nearest neighbor signals? If the Q-level is set at 14% or above, the answer is no (since 103/90.5=13.8%), and therefore the pattern value at channel 6 at the 14% Q-level for wool is set at "0" (see Table 1 below). If the Q-level is set at 12% or below, however, the answer is yes (since 103/90.5=13.8%, which is higher than 12%), and therefore the pattern value at channel 6 for the 12% Q-level is set at "1" (see Table 1). As can be seen, the smaller the Q-level, the greater is the amount of spectral detail that will be noticed. The ten channels of the sensor array permit this process to be repeated for all six decision channels. The outer channels ("a, b, c and d") merely supply necessary data for the outer four decision channels ("1, 2, 5 and 6").

Table 1 lists the pattern values for wool at the factory-set calibration of the sensor array. A minus value (−1) means that the signal of the respective channel is at least Q% smaller than the average of the two next-nearest neighbor channels.

TABLE 1

| Q-level (%) | Pattern values for the decision channels: | | | | | |
|---|---|---|---|---|---|---|
| | 1 | 2 | 3 | 4 | 5 | 6 |
| 14 | 0 | 0 | 0 | 0 | 0 | 0 |
| 12 | 0 | 0 | 0 | 0 | 0 | 1 |
| 10 | 0 | 0 | 0 | 0 | 0 | 1 |
| 8 | 0 | −1 | 0 | 0 | 1 | 1 |
| 6 | 0 | −1 | 0 | 0 | 1 | 1 |
| 5 | 0 | −1 | 0 | 0 | 1 | 1 |
| 4 | −1 | −1 | 0 | 0 | 1 | 1 |
| 3 | −1 | −1 | 0 | 0 | 1 | 1 |

As can be seen, at the high Q-levels, only channel 6 recognizes the drop-off at 1900 nm (at the 12% Q-level), as shown in FIG. 1, but at the lower Q-levels, not only does channel 5 recognize the drop-off at 1900 nm (at the 8% Q-level), but the absorption dip at 1500 nm is also recognized, first by channel 2 (at the 8% Q-level) and then by channel 1 (at the 4% Q-level).

As will be recognized by those skilled in the art, system response may change over the life of the apparatus, or due to changing ambient conditions. For example, any of various factors, such as the spectrum of the light source or the sensitivity of the photoconductive cells, may change or vary over the life of the apparatus. Any such changes or variations may cause a change in the average slopes of the diffuse-reflectance spectra (as shown in FIGS. 1 and 2 for wool and cotton, respectively). One advantage of the present invention is that it compensates for such variations preferably by providing the following two additional tables of reference pattern values for each material of interest. Table 2 lists the pattern values of wool when the spectrum of FIG. 1 drops exponentially by a factor of 3 between 1200 and 2000 nm.

TABLE 2

| Q-level (%) | Pattern values for the decision channels: | | | | | |
|---|---|---|---|---|---|---|
| | 1 | 2 | 3 | 4 | 5 | 6 |
| 14 | 0 | 0 | 0 | 0 | 0 | 0 |
| 12 | 0 | −1 | 0 | 0 | 0 | 0 |
| 10 | 0 | −1 | 0 | 0 | 0 | 0 |
| 8 | 0 | −1 | 0 | 0 | 0 | 1 |
| 6 | −1 | −1 | 0 | 0 | 0 | 1 |
| 5 | −1 | −1 | 0 | 0 | 0 | 1 |
| 4 | −1 | −1 | 0 | 0 | 0 | 1 |
| 3 | −1 | −1 | 0 | 0 | 1 | 1 |

Table 3 considers the other extreme; when the response rises exponentially by a factor of 3 between 1200 and 2000 nm.

TABLE 3

| Q-level (%) | Pattern values for the decision channels: | | | | | |
|---|---|---|---|---|---|---|
| | 1 | 2 | 3 | 4 | 5 | 6 |
| 14 | 0 | 0 | 0 | 0 | 0 | 0 |
| 12 | 0 | 0 | 0 | 0 | 0 | 1 |
| 10 | 0 | 0 | 0 | 0 | 0 | 1 |
| 8 | 0 | −1 | 0 | 0 | 1 | 1 |
| 6 | 0 | −1 | 0 | 0 | 1 | 1 |
| 5 | −1 | −1 | 0 | 0 | 1 | 1 |
| 4 | −1 | −1 | 0 | −1 | 1 | 1 |
| 3 | −1 | −1 | 0 | −1 | 1 | 1 |

As can be seen, there are obvious differences among the three tables of pattern values, however, all have either a "+1" in either or both channels 5 and 6, and a "−1" in channel 2 at the 8% Q-level and below. Based on this type of empirical evidence, it has been determined that none of the other fabrics of interest exhibit this type of response. Accordingly, this channel pattern alone (a "+1" in channel 6 at the 6% Q-level or above) is sufficient to identify wool. In addition, a significant advantage of the present invention is that wool (or another diffusely-reflecting material) can still be identified when the system response spectrum tilts by factors of three one way or the other with respect to the "ideal" factory-set, flat condition. These three tables are generated for each fabric of interest, and stored in memory for comparison to the corresponding pattern values for each unknown fabric to identify the unknown fabric, as is described further below.

Figure 8A:
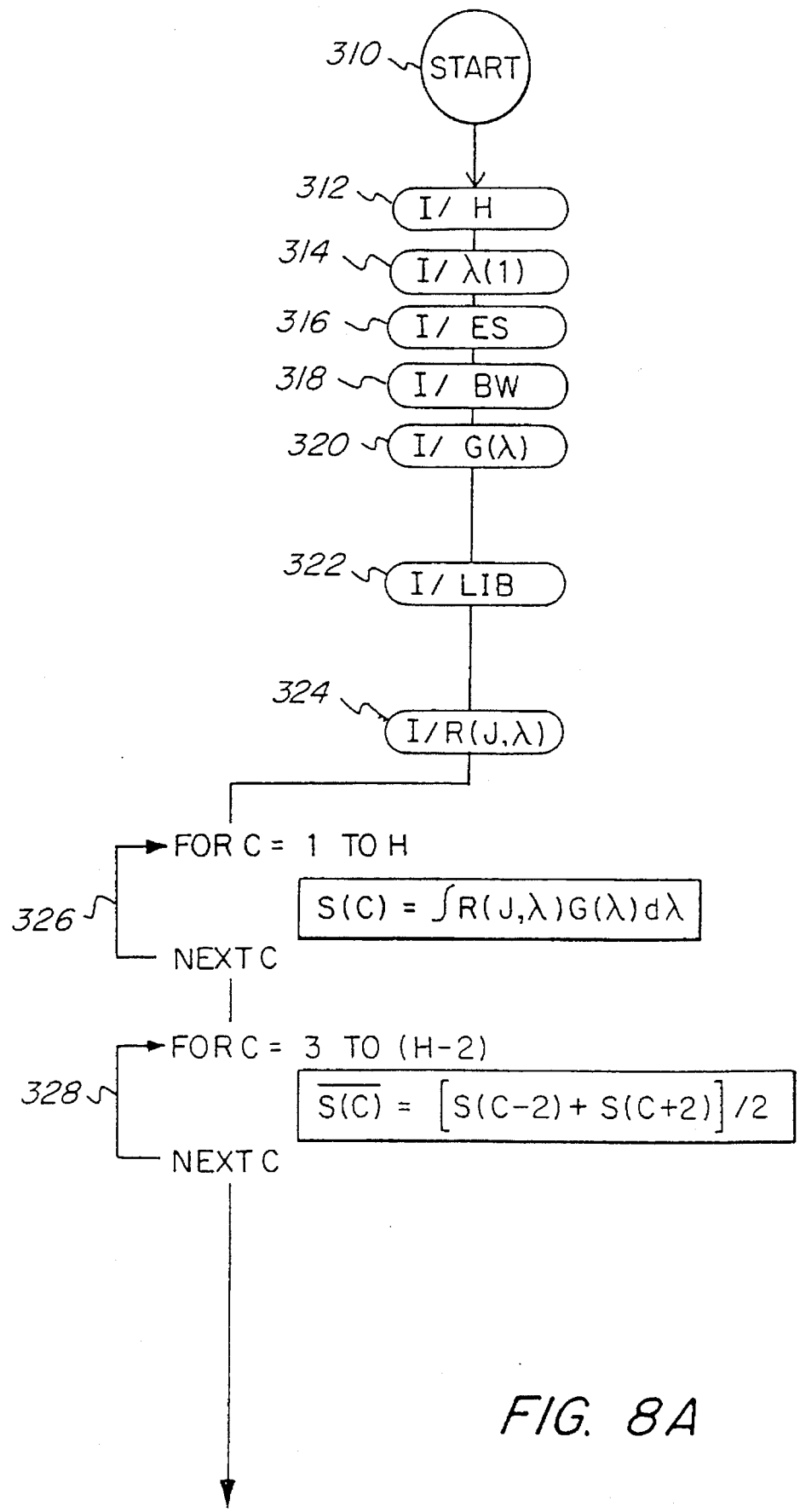
FIGS. 8A and 8B are a flow chart illustrating conceptually a method of the present invention for deciding by computation whether the reflection spectrum of an unknown fabric (or other diffusely-reflecting material) matches that of any known reference fabrics in order to identify the unknown fabric.
Figure 8B:
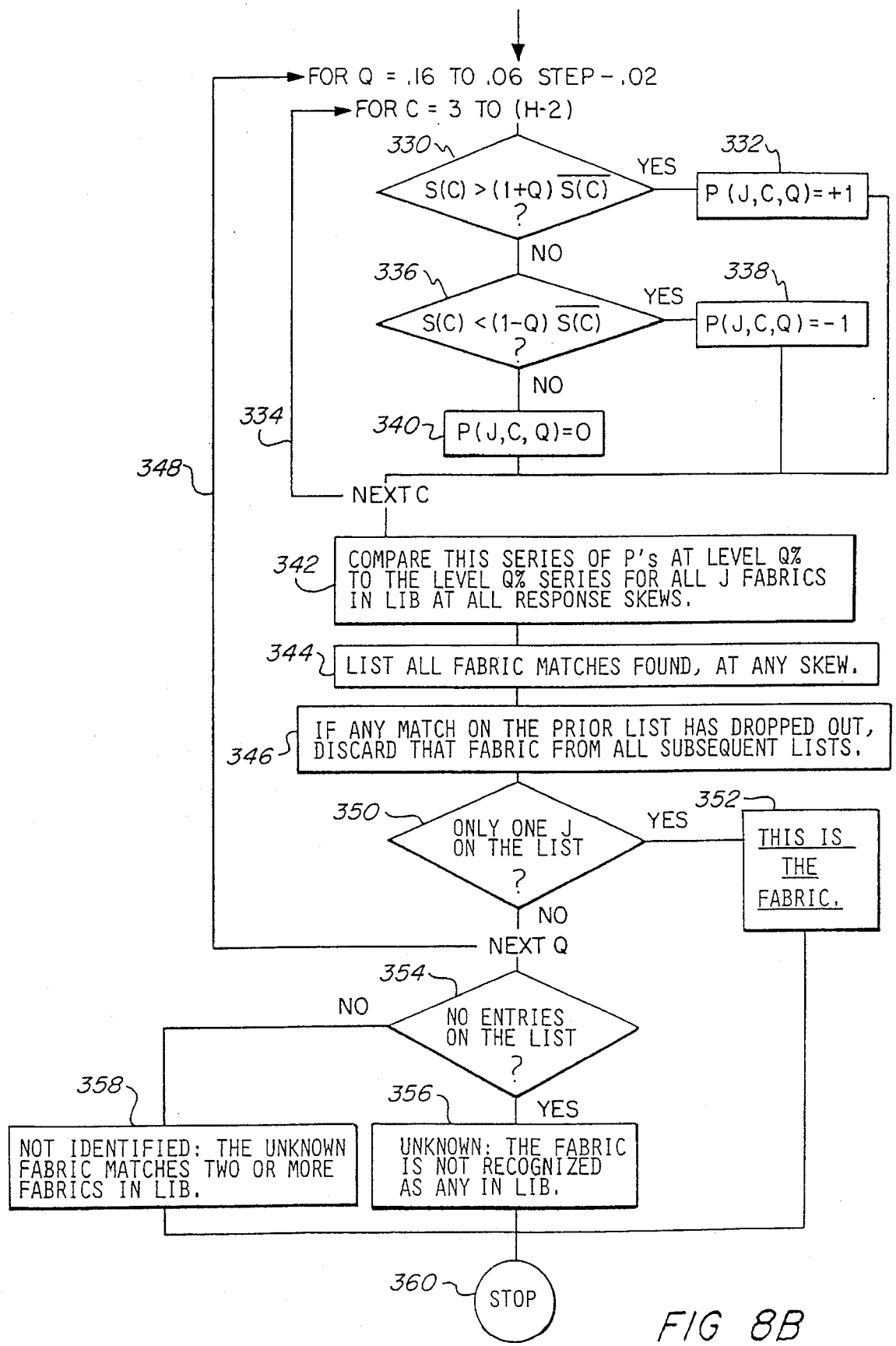

Turning to FIGS. 8A and 8B, a flow chart illustrates conceptually the method of the present invention for determining whether the reflection spectrum as indicated by the pattern values of an unknown fabric (or other diffusely-reflecting material) matches that of any of J known fabrics (or other diffusely-reflecting materials) stored in memory (LIB), in order to identify the unknown fabric. The starting point is step 310, and the next four steps indicate the input of parameters and constants for fabric identification in accordance with this embodiment of the present invention. Step 312 is the input of the number of sensor channels (or photoconductive cells) of the sensor array, i.e., C=1, 2, . . ., H, and in this embodiment of the present invention, H=10 (6 decision channels, and 4 outer channels). Step 314 is the input of the wavelength of the first channel (e.g., in FIGS. 1 and 2, the wavelength of the first channel ("a") is 1290 nm). The next input is the bandwidth separation of the channels ("ES"), as indicated by step 316, and the half-height bandwidth of the channels ("BW"), as indicated by step 318. In the embodiment of the present invention illustrated, ES is approximately 80 nm and BW is approximately 40 nm. The response spectrum of any channel is also input, as indicated by step 320.

A library (LIB) of fabric response patterns, which essentially includes the three tables as illustrated above for wool, for each of the J fabrics of interest, is also input into memory (LIB), as indicated by step 322. As the radiation is transmitted onto the unknown fabric, and the diffusely reflected radiation is received by the sensor array, the sensor array transmits its ten output signals R(j,λ) to the processor, as indicated by step 324. The signal S(C) from each channel is analog integrated over the channel bandwidth by the interference filter/amplifier built into each channel of the sensor array; this integration is represented here by the computational DO-loop for receiving and storing each integrated signal S(C), as indicated by step 326. Then, for each channel, the processor calculates the average of the signals of the two next-nearest neighbors of the respective channel, $\overline{S(C)}$, as indicated by step 328.

The processor then computes the pattern values for each decision channel (C=3 to (H-2)) at selected Q-levels, and compares the pattern values at each Q-level to every corresponding reference pattern value at that respective Q-level stored in the library (LIB). At step 330, the processor determines whether the signal from each respective channel S(C) is more than Q% higher than the average of the signals of the two next-nearest neighbors (S(C)>(1+Q)$\overline{S(C)}$?). If the answer is yes (Y), then a "+1" pattern value is assigned to that respective channel (P(j,C,Q)=1), as indicated by step 332, and the processor moves on to make the same determination for the next channel C, as indicated by the loop 334. If the answer is no (N), the processor then determines if the signal from the respective channel S(C) is less than Q% lower than the average of the signals of the two next-nearest neighbors (S(C)<(1−Q)$\overline{S(C)}$?), as indicated by step 336. If the answer is yes (Y), then a "−1" pattern value is assigned to that respective channel (P(j,C,Q)=−1), as indicated by step 338, and the processor moves on to make the same determinations for the next channel C, as indicated by the loop 334. If the answer is no (N), then a pattern value of "0" is assigned to that respective channel (P(j,C,Q)=0), as indicated by step 340. The processor then repeats this decision process for each channel C at that respective Q-level, as indicated by the loop 334.

Once the pattern values (P(j,C,Q)) are determined for each channel (C=3 to (H-2)) at a respective Q-level, the processor compares them to the corresponding pattern values at the same Q-level for each reference fabric J in the library (LIB) at all response skews (i.e., the pattern values in each of the three tables, as described above), as indicated by step 342. The processor then lists the reference fabrics J for all matches that are found for each respective decision channel C, as indicated by step 344. If any match on a prior list for a respective decision channel (i.e., a match at a previous Q-level) is not found, then it is deleted from the list of matching reference fabrics J, as indicated by step 346.

Figure 7:
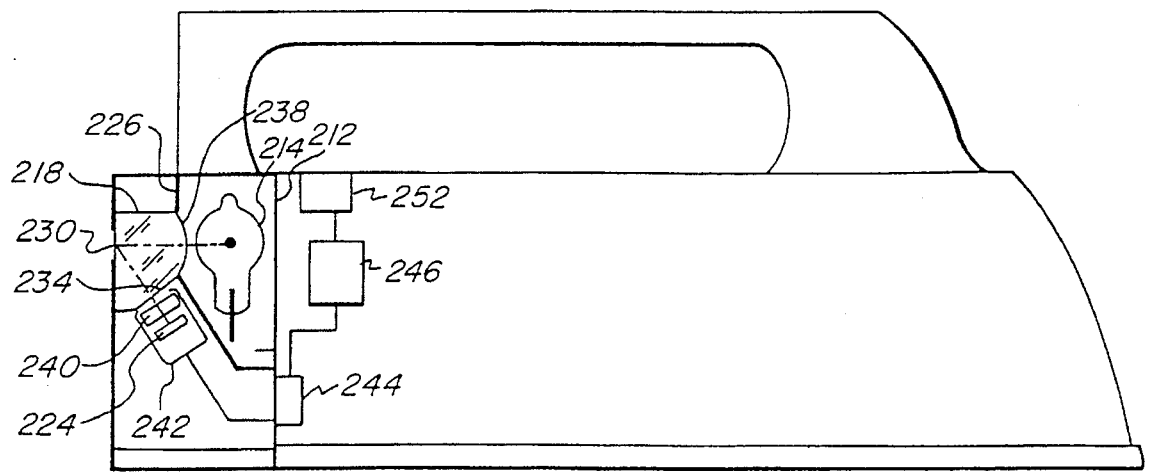
FIGS. 7 is a schematic illustration of another embodiment of an apparatus embodying the present invention, in which components of the apparatus of FIG. 6 are mounted within a household iron to identify the type of fabric being ironed, and to control the temperature of the iron based on this identification.

This entire process of assigning pattern values (P(j,C,Q)) to each decision channel, and comparing the assigned values to the reference values at the same Q-level, is repeated for each selected Q-level, as indicated by the loop 348. In the embodiment of the present invention illustrated, the selected Q-levels are from 0.16 to 0.06, with a −0.02 increment from one Q-level to the next, as indicated by the loop 348. In this embodiment of the present invention, this loop is repeated at most 6 times, generating six successive lists of matches. If at any time during these repetitions it is determined that only one matching reference fabric remains on a list, as indicated by step 350, then the unknown fabric is positively identified as that particular fabric, as indicated by step 352. This result can be transmitted onto a display, as illustrated in FIG. 6, or used to control a thermostat on a household iron, for example, as illustrated in FIG. 7. Once the unknown fabric is identified, the processor stops, as indicated by step 360, until a new set of signals are transmitted by the sensor array to identify another unknown fabric.

It is logically possible that in some cases this procedure may not be able to make a positive identification of the unknown diffusely-reflecting material with respect to any one of the sets of pattern values stored in the reference library. If the DO-loop 348 is completed and the processor determines at step 350 that either no fabric name is left on the final list, or two or more fabric names are on the final list, it moves to step 354. If there is no entry on the final list (Y), then the sample fabric, or other reflecting material, is unknown to any of the reference materials in the processor library; its spectral reflectance curve is significantly different from that of any of the fabrics or materials used to form the processor library. Consequently, it is unrecognized, as indicated by step 356.

If, on the other hand, there are two or more fabric matches indicated on the final list at step 354 (N), then the unknown fabric's infrared spectrum is sufficiently close to those of two or more of the library's fabric spectra that positive identification with one of them is impossible, at least at the 6% Q-level of significance for H decision channels, as indicated by step 358. In this situation, the several possible fabrics can be transmitted onto a display, as illustrated in FIG. 6, or used to control a household iron, as illustrated in FIG. 7. For example, if the two or more possible fabrics are all polyester blends, then the iron can be automatically adjusted to a selected temperature for all polyester blends.

It is noted that the 10 channel array described above is purely exemplary, and any number of channels can be employed as needed. For example, it may be desirable to employ more than 10 channels to reduce the possibility of matches with multiple reference fabrics. It may be equally desirable, however, to reduce the number of channels, if the apparatus is only going to be required to distinguish between a more limited number of fabrics, or other diffusely-reflecting materials. In addition, the sensor array can be designed to receive diffusely-reflected radiation anywhere within a predetermined wavelength range, which at its outer limits, is greater than 1000 nm and less than 2500 nm.

One advantage of the method of the present invention is that because the signal value from each channel of the sensor array is compared with the average value of the signal values for the two next-nearest neighbors of the respective channel, the pattern values should be reasonably stable against changes in the overall response spectrum of the sensor array over time, changes in the spectrum of the light source, or due to changes in ambient conditions. The system is therefore able to operate over time without the need to check the "white" reading of the sensor array that is set at the factory, while at the same time facilitate the ability to more reliably distinguish one fabric (or other diffusely-reflecting material) from another. This feature permits fabric identification that does not easily get thrown off by long term drifts in the spectrum of the light source, or by changes in the IR-sensitivity of the sensor array. These are significant advantages in providing a trouble-free, commercially feasible device.

Another advantage of the present invention is that because it employs diffuse reflectance, preferably within the range of approximately 1200 to 2400 nm, to determine the identity and/or composition of an unknown material, low-cost, conventional subminiature tungsten light sources can be used to generate the radiation. In addition, in this wavelength range, relatively low-cost photoconductive sensors, such as the PbS sensor array described above, can be employed to detect the intensity of the diffusely-reflected radiation at each selected bandwidth of interest. Moreover, most dyes employed in textile fabrics are non-absorbing in the infrared, and therefore the color of a fabric (or other diffusely-reflecting material) will not affect the ability of the method and apparatus of the present invention to identify the unknown material. Yet another advantage of the present invention is that because only low-resolution band spectroscopy is needed to identify fabrics, relatively low-cost, high-dispersion/low-resolution gratings, or wide-bandwidth interference filters, as also described above, can provide adequate spectral signatures, thus facilitating a designer's ability to make a low-cost, commercially feasible device. Indeed, the apparatus of the present invention can be employed within a typical household appliance without significant additional expense, such as an iron, as illustrated in FIG. 7. A significant advantage of this embodiment is that the temperature of the iron can be automatically controlled based on the type of fabric being ironed (without the user even knowing what type of fabric is being ironed).

I claim:

1. A method for identifying an unknown diffusely-reflecting reference material, comprising the following steps:

establishing a library of pattern values for a plurality of reference materials;

determining the pattern values for the reference materials by generating a plurality of signals indicative of diffuse-reflection characteristics of the reference materials within a defined wavelength channel of finite bandwidth, and comparing the value of a signal of the respective channel to another value based on the average of the values of the signals of the two next-nearest neighbor channels;

transmitting radiation from a light source onto the unknown material;

receiving at least a portion of the radiation diffusely-reflected by the unknown material with a detector and generating signals indicative of diffuse-reflection characteristics of the unknown material within a defined wavelength channel of finite bandwidth;

comparing the value of the signal of the respective channel to another value based on the average of the values of the signals of the two next-nearest neighbor channels to generate pattern values for the unknown material; and comparing the pattern values for the reference materials to corresponding pattern values for the unknown material to identify the unknown material.

2. A method as defined in claim 1, further comprising the step of generating a plurality of pattern values for each channel, wherein each pattern value is based on a respective Q-level, and each Q-level defines a range of values above and below each respective channel signal.

3. A method as defined in claim 2, wherein each pattern value is based on whether the average value of the signals of the two next-nearest channels falls within the range defined by the respective Q-level of the respective channel signal.

4. A method as defined in claim 1, further comprising the step of automatically controlling the temperature of a household iron based on the identification of the material.

5. A method as defined in claim 1, wherein the material is a textile fabric, and the radiation received by the detector is within the range of approximately 1200 to 2200 nm.

6. A method as defined in claim 1, further comprising the step of generating three sets of pattern values for each reference material.

* * * * *